United States Patent
Aubry et al.

(10) Patent No.: US 6,956,137 B1
(45) Date of Patent: Oct. 18, 2005

(54) SINGLET OXYGEN OXIDATION OF ORGANIC SUBSTRATES

(75) Inventors: Jean-Marie Aubry, Oignies (FR); Veronique Rataj-Nardello, Villeneuve d'Ascq (FR); Paul Alsters, Maastricht (NL)

(73) Assignee: DSM Fine Chemicals Austria NFG GmbH & CO KG, Linz (AT)

( * ) Notice: Subject to any disclaimer, the term of this patent is extended or adjusted under 35 U.S.C. 154(b) by 0 days.

(21) Appl. No.: 09/937,724

(22) PCT Filed: Mar. 23, 2000

(86) PCT No.: PCT/EP00/02552

§ 371 (c)(1),
(2), (4) Date: Sep. 28, 2001

(87) PCT Pub. No.: WO00/61524

PCT Pub. Date: Oct. 19, 2000

(30) Foreign Application Priority Data

Apr. 13, 1999 (AT) .................................... 647/99

(51) Int. Cl.$^7$ .................... C07C 409/06; C07C 409/02; C07C 409/04; C07C 409/08; C07C 409/20
(52) U.S. Cl. .................. 568/569; 568/469.9; 568/558; 568/567; 568/568; 568/577
(58) Field of Search ............................ 568/569, 469.9, 568/558, 567, 568, 577

(56) References Cited

OTHER PUBLICATIONS

Aubry, J. Am. chem. Soc., 1985, vol. 107, pp. 5844-5849.*
Barton et al., J. Chem. Soc. Perkin Transactions 1, 1975, pp. 610-1614.*
Barton et al., J. Chem. Soc., Perkin Transactions 1, 1975, pp. 1610-1614.*
Van Laar et al., Chem. Commun., 1998, pp. 267-268.*
Barton, Journal of the Chemical Society, Perkin Transactions 1, pp. 1610-1614 (1975).
Van Laar, Journal of the Chemical Society, Chemical Communications, pp. 267-268 (1998).
Aubry, Journal of the American Chemical Society, vol. 119, No. 23, pp. 5286-5294 (1997).
Aubry, Journal of Organic Chemistry, vol. 54, No. 3, pp. 726-728 (1989).

* cited by examiner

*Primary Examiner*—Elvis O. Price
(74) *Attorney, Agent, or Firm*—Wenderoth, Lind & Ponack, L.L.P.

(57) ABSTRACT

The invention relates to a method for oxidizing organic substrates using $^1O_2$ in which hydrophobic organic substrates that react with $^1O_2$ are added to an organic solvent in the presence of a heterogeneous or homogeneous catalyst with 30–70% being compr Afterwards, $H_2O_2$ is catalytically decomposed into water and $^1O_2$, and the oxidation into corresponding oxidation products ensues.

5 Claims, No Drawings

SINGLET OXYGEN OXIDATION OF ORGANIC SUBSTRATES

The only singlet oxygen oxidation ($^1O_2$—Ox) which is currently carried out industrially is the photochemical $^1O_2$—Ox in which the $^1O_2$ is generated by a photochemical route. The disadvantage of this process is given by the high costs of the photochemical equipment required, and by a limited service life. The required lamps degenerate relatively rapidly during the oxidation as a result of soiling of the glass surface. In addition, this process is not suitable for colored substrates. The process is actually suitable only for fine chemicals which are prepared on a relatively small scale. (La Chimica e l'Industria, 1982, Vol. 64, page 156).

For this reason, attempts have been made to find other process variants for the $^1O_2$—Ox which are suitable for the $^1O_2$—Ox of non-water-soluble, hydrophobic organic substrates.

J. Am. Chem. Soc., 1968, 90, 975 describes, for example, the classical "dark" $^1O_2$—Ox in which $^1O_2$ is not generated photochemically, but chemically. In this process, hydrophobic substrates are oxidized by means of a hypochlorite/$H_2O_2$ system in a solvent mixture of water and organic solvent. However, this process has only found a few synthetic applications since many substrates are only sparingly soluble in the required medium. In addition, the use possibility is rather limited because of secondary reactions between hypochlorite and substrate or solvent. In addition, a large part of the $^1O_2$ is deactivated in the gas phase. In addition, this process is not suitable for industrial scale since in the organic medium addition of the hypochlorite onto $H_2O_2$ results, and a large excess of $H_2O_2$ is required to suppress the secondary reaction of substrate with hypochlorite. An additional disadvantage arises as a result of the formation of stoichiometric amounts of salt.

A variant of the "dark" $^1O_2$—$O_x$, which is not based on hypochlorite and thus should partly avoid the above disadvantages, is known, for example, from J. Org. Chem., 1989, 54, 726 or J. Mol. Cat., 1997, 117, 439, according to which some water-soluble organic substrates are oxidized with $H_2O_2$ and a molybdate catalyst in water as solvent. According to Membrane Lipid Oxid. Vol. II, 1991, 65, the $^1O_2$—Ox of water-insoluble, organic substrates with the molybdate/$H_2O_2$ system is difficult since it was assumed that none of the customary solvents is suitable for maintaining the disproportionation, catalyzed by molybdate, of $H_2O_2$ into water and $^1O_2$. As is described in Membrane Lipid Oxid. Vol. II, 1991, 65, water-insoluble substrates, such as, for example, α-terpinene or β-citronellol, can be oxidized with the molybdate/$H_2O_2$ system in a MeOH/water mixture (70/30) with only relatively low yields of 70%. As well as the only moderate yields which are obtained using MeOH/water, the very small application spectrum of this method based on aqueous solvent mixtures is an additional disadvantage since this method, as is clear from J. Am. Chem. Soc., 1997, 119, 5286, is limited to somewhat hydrophilic substrates or to hydrophobic substrates with a low molecular weight.

J. Am. Chem. Soc., 1997, 119, 5286 and EP-A-0 288 337 describes a process that permits the generation, catalyzed by molybdate in aqueous solution, of $^1O_2$ from $H_2O_2$ and is nevertheless suitable for hydrophobic substrates from a relatively wide molecular weight range. In this process, a microemulsion is used as reaction medium. However, use on an industrial scale is associated with problems since product isolation from the microemulsion is difficult. In addition, it is a relatively expensive process since rather large amounts of surfactant have to be used relative to the substrate.

Accordingly, it was an object of the present invention to find an improved method of the "dark" $^1O_2$—Ox which can be used simply, cost-effectively and in an environmentally friendly manner on an industrial scale and is suitable for a large number of substrates.

Unexpectedly, it has now been found that the "dark" $^1O_2$—Ox can be carried out in an extremely efficient manner with high yield in certain organic solvents as reaction medium, without the addition of water as cosolvent and without surfactant.

Accordingly, the present invention provides a process for the oxidation of organic substrates by means of $^1O_2$, which comprises adding 30–70% strength $H_2O_2$ to hydrophobic organic substrates which react with $^1O_2$ in an organic solvent in the presence of a heterogeneous or homogeneous catalyst, whereupon, following the catalytic decomposition of $H_2O_2$ to give water and $^1O_2$, oxidation to give the corresponding oxidation products takes place.

The process according to the invention is suitable for the oxidation of hydrophobic organic substrates which react with $^1O_2$.

Accordingly, substrates which may be used are the following compounds: olefins which contain one or more, i.e. up to 10, preferably up to 6, particularly preferably up to 4, C=C double bonds; electron-rich aromatics, such as $C_6$–$C_{50}$, preferably up to $C_{30}$, particularly preferably up to $C_{20}$, phenols, polyalkylbenzenes, polyalkoxybenzenes; polycyclic aromatics having 2 o 10, preferably up to 6, particularly preferably up to 4 aromatic rings; sulfides, such as, for example, alkyl sulfides, alkenyl sulfides, aryl sulfides which are either mono- or disubstituted on the sulfur atom, and heterocycles having an O, N or S atom in the ring, such as, for example, $C_4$–$C_{50}$, preferably up to $C_{30}$, particularly preferably up to $C_{20}$, furans, $C_4$–$C_{50}$, preferably up to $C_{30}$, particularly preferably up to $C_{20}$, pyrroles, $C_4$–$C_{60}$, preferably up to $C_{30}$, particularly preferably up to $C_{20}$, thiophenes. In this connection, the substrates may have one or more substituents, such as halogen (F, Cl, Br, I), cyanide, carbonyl groups, hydroxyl groups, $C_1$–$C_{50}$, preferably up to $C_{30}$, particularly preferably up to $C_{20}$, alkoxy groups, $C_1$–$C_{50}$, preferably up to $C_{30}$, particularly preferably up to $C_{20}$, alkyl groups, $C_6$–$C_{50}$, preferably up to $C_{30}$, particularly preferably up to $C_{20}$, aryl groups, $C_2$–$C_{50}$, preferably up to $C_{30}$, particularly preferably up to $C_{20}$, alkenyl groups, $C_2$–$C_{50}$, preferably up to $C_{30}$, particularly preferably up to $C_{20}$, alkynyl groups, carboxylic acid groups, ester groups, amide groups, amino groups, nitro groups, silyl groups, silyloxy groups, sulfone groups, sulfoxide groups. In addition, the substrates may be substituted by one or more $NR^1R^2$ radicals in which $R^1$ or $R^2$ may be identical or different and are H; $C_1$–$C_{50}$, preferably up to $C_{30}$, particularly preferably up to $C_{20}$, alkyl; formyl; $C_2$–$C_{50}$, preferably up to $C_{30}$, particularly preferably up to $C_{20}$, acyl; $C_1$–$C_{50}$, preferably up to $C_{30}$, particularly preferably up to $C_{20}$, benzoyl, where $R^1$ and $R^2$ may also together form a ring, such as, for example, in a phthalimido group.

Examples of suitable substrates are: 2-butene; isobutene; 2-methyl-1-butene; 2-hexene; 1,3-butadiene; 2,3-dimethylbutene; $\Delta^{9,10}$-octalin, 2-phthalimido-4-methyl-3-petene; 2,3-dimethyl-1,3-butadiene; 2,4-hexadiene; 2-chloro-4-methyl-3-pentene; 2-bromo-4-methyl-3-pentene; 1-trimethylsilylcyclohexene; 2,3-dimethyl-2-butenyl-para-tolylsulfone; 2,3-dimethyl-2-butenyl-para-tolyl sulfoxide; N-cyclohexenylmorpholine; 2-methyl-2-norbornene; terpinolene; α-pinene; β-pinene; β-citronellol; ocimene, citronellol; geraniol; farnesol; terpinene; limonene; trans-2,3-dimethylacrylic acid; α-terpinene; isoprene; cyclopentadiene; 1,4- diphenylbutadiene; 2-ethoxybutadiene; 1,1'-dicyclohexenyl; cholesterol; ergosterol acetate; 5-chloro-1,3-cyclohexadiene; 3-methyl-2-buten-1-ol; 3,5,5-trimethylcyclohex-2-en-1-ol; phenol, 1,2,4-trimethoxybenzene, 2,3,6-trimethylphenol, 2,4,6-trimethylphenol, 1,4-dimethylnaphthalene, furan, furfuryl alcohol, furfural, 2,5-dimethylfuran, isobenzofuran, dibenzyl sulfide, (2-methyl-5-tert-butyl)phenyl sulfide, etc.

As a result of the oxidation according to the invention, the corresponding oxidation product is obtained from the substrates. Alkenes, (polycyclic) aromatics or heteroaromatics give, in particular, hydroperoxides or peroxides which are able to further react under the reaction conditions to give alcohols, epoxides, acetals or carbonyl compounds, such as ketones, aldehydes, carboxylic acids or esters, if the hydroperoxide or the peroxide is unstable.

The oxidation according to the invention is carried out in an organic solvent.

Suitable solvents are $C_1$–$C_8$-alcohols, such as methanol, ethanol, propanol, isopropanol, butanol, isobutanol; ethylene glycol, propylene glycol, formamide, N-methylformamide, dimethylformamide, sulfolane, propylene carbonate.

Preference is given to using methanol, ethanol, propanol, isopropanol, ethylene glycol, propylene glycol, formamide, N-methylformamide or dimethylformamide, particularly preferably methanol, ethanol, ethylene glycol, propylene glycol, formamide or dimethylformamide as solvent.

Up to 25% of water may optionally be added to the organic solvent. However, the addition of water does not bring any advantages for the reaction. Water is therefore preferably not added.

A metal which is suitable for $^1O_2$ oxidations and is described, for example, in J. Am. Chem. Soc., 1985, 107, 5844 or in Membrane Lipid Oxid. Vol. II, 1991, 65, is added as heterogeneous or homogeneous inorganic catalyst to the solvent/substrate mixture.

In this connection, the metal can be in forms customary for $^1O_2$ oxidations, for example as the oxide, oxo complex, nitrate, carboxylate, hydroxide, carbonate, chloride, fluoride, sulfate, tetrafluoroborate, etc. Preference is given to catalysts based on molybdenum, tungsten, scandium, vanadium, titanium, zirconium, praseodymium, neodymium, samarium, europium, terbium, dysprosium, holmium, erbium, ytterbium and lutetium. Particular preference is given to molybdenum catalysts.

The amount of catalyst used depends on the substrate used and is between 1 and 50 mol %, preferably between 5 and 25 mol %.

This is followed by the addition of 30–70% strength, preferably 40–60% strength, $H_2O_2$. $H_2O_2$ is preferably added slowly or in portions to the reaction mixture of solvent, substrate and catalyst, the reaction mixture being stirred.

In the process according to the invention, the consumption of $H_2O_2$ is dependent on the substrate used. For reactive substrates, 2 to 3 equivalents of $H_2O_2$ are preferably needed, while less reactive substrates are preferably reacted with 3 to 10 equivalents of $H_2O_2$.

The reaction temperature is between 0 and 50° C., preferably between 15 and 35° C.

In some cases, to improve activation of the catalyst, it may be advantageous to add customary basic or acidic additives to the reaction mixture.

The course of the reaction can be monitored by means of UV spectroscopy or by means of HPLC. When the reaction is complete, i.e. after 1 to 30 hours, depending on the reaction conditions, the reaction mixture is worked up. Removal of the catalyst has proven unexpectedly simple particularly when molybdate catalysts are used, such as e.g. sodium molybdate, in some solvents. Although the reaction proceeds completely homogeneously when molybdate catalysts, such as, for example, $Na_2MoO_4.2H_2O$ in monohydroxylic, alcoholic solvents, i.e. in monohydric alcohols such as, for example, methanol or ethanol, are used, provided $H_2O_2$ is added, the catalyst, after all of the $H_2O_2$ has been added, precipitates out of the reaction mixture, as a result of which the catalyst can be separated off by simple centrifugation or filtration, and recycled.

The end-product which remains can, where appropriate, be purified by means of recrystallization, extraction or distillation.

The process according to the invention permits the oxidation of a large number of hydrophobic compounds and is particularly advantageous for the oxidation of water-insoluble substrates which could not be oxidized with hitherto known chemical methods with high yield. Accordingly, the process according to the invention is particularly suitable for the oxidation of unsaturated organic compounds, such as terpenes, for example α-terpinene and citronellol, aromatic polycycles, steroids, furans, cyclopentadienes, phenols etc., and generally for all compounds which react with $^1O_2$.

The process according to the invention gives the desired end-products in high yields of up to 100% with high purity.

The process according to the invention is characterized by the simple process regime which is best suited to the industrial scale since it can take place in simple multipurpose plants and with simple work-up steps, and can be used for a wide spectrum of substrates.

EXAMPLE 1 a) 0.2 ml of an aqueous 2 mol/l $Na_2MoO_4$ solution or
b) 0.4 mmol of $Na_2MoO_4.2eq$.

were added to a thermostated solution (25° C.) of 2 mmol of an organic substrate (α-terpinene or β-citronellol) in 4 ml of an organic solvent. 0.08 ml of $H_2O_2$ (50%) were added to this mixture. After the reaction mixture had turned yellow again, two further 0.08 ml portions of $H_2O_2$ (50%) were added. The course of the reaction was monitored in the case of α-terpinene by means of UV spectroscopy (266 nm) and in the case of β-citronellol by means of HPLC (MeOH/$H_2O$ 70/30).

EXAMPLE 2 a) 0.2 ml of an aqueous 2 mol/l $Na_2MoO_4$ solution or
b) 0.4 mmol of $Na_2MoO_4.2eq$.

were added to a thermostated solution (25° C.) of 2 mmol of an organic substrate (α-terpinene or β-citronellol) in 4 ml of an organic solvent. 0.25 ml of $H_2O_2$ (50%) were added to this mixture in one portion. The course of the reaction was monitored in the case of α-terpinene by means of UV spectroscopy (266 nm) and in the case of β-citronellol by means of HPLC (MeOH/$H_2O$ 70/30).

The solvents used and the conversion of α-terpinene into ascaridol and β-citronellol into a 1/1 mixture of the corresponding hydroperoxides are given in table 1:

TABLE 1

| Example | Substrate | Solvent | Cat. a) or b) | Conversion |
|---|---|---|---|---|
| 1 | α-terpinene | Methanol | a | 100% after 2 h |
| 1 | α-terpinene | Methanol | b | >95% after 2 h |
| 2 | α-terpinene | Methanol | a | >95% after 2 h |
| 1* | α-terpinene | Ethanol | a | 90% after 22 h |
| 1 | α-terpinene | Formamide | a | 70% after 21 h |
| 1 | α-terpinene | N-Me-formamide | a | 75% after 3 h |

TABLE 1-continued

| Example | Substrate | Solvent | Cat. a) or b) | Conversion |
|---|---|---|---|---|
| 1 | α-terpinene | DMF | a | 64% after 21 h |
| 1 | α-terpinene | Sulfolane | a | 70% after 21 h |
| 1 | β-citronellol | Methanol | a | 80% after 3 h |
| 1 | β-citronellol | Formamide | a | 95% after 3 h |

*3rd portion of $H_2O_2$ was 0.09 ml

EXAMPLE 3

Product Isolation from Reaction Mixture with Methanol as Solvent

After the time given in table 1, the precipitated-out catalyst was removed from the reaction mixture by means of centrifugation. The precipitate was washed twice with absolute ethanol, and the combined solvent batches (methanol and ethanol) were removed on a rotary evaporator. The oxidation product which remained was dissolved in $CDCl_3$ for NMR analysis. In the case of α-terpinene, analysis confirmed the formation of a virtually quantitative amount of >95% pure ascaridol. In the case of β-citronellol, approximately 80% of product were obtained which, according to NMR analysis, consisted of a 1/1 mixture of the two corresponding hydroperoxides.

EXAMPLE 4

At 35° C., 45 μl of $H_2O_2$ (50%) were added to a solution of 325 μl of α-terpinene and 48.5 mg of $Na_2MoO_4 \cdot 2H_2O$ in 4 ml of methanol. Five further 45 μl portions of $H_2O_2$ (50%) were added to this mixture as soon as the red-colored reaction mixture turned yellow again. After 1.5 hours, the reaction mixture was analyzed by means of HPLC. Analysis gave a quantitative formation of ascaridol.

EXAMPLE 5

At 25° C., 80 μl of $H_2O_2$ (50%) were added to a solution of 365 μl of citronellol and 97 mg of $Na_2MoO_4 \cdot 2H_2O$ in 4 ml of ethylene glycol. After 1, 2 and after 19 hours, 3 further 80 μl portions of $H_2O_2$ (50%) were added to this mixture. HPLC analysis gave a 100% conversion with a yield of secondary hydroperoxide of 38% and a yield of tertiary hydroperoxide of 62%.

What is claimed is:

1. A process for the oxidation of organic substrates by means of $^1O_2$, which consists of adding 40–60% strength $H_2O_2$ to hydrophobic organic substrates which react with $^1O_2$ in a monohydric $C_1$–$C_8$ alcohol as a solvent in the presence of 5–25 mol % of a homogeneous molybdate catalyst, whereupon $H_2O_2$ is catalytically decomposed to give water and $^1O_2$, oxidizing said substrate to the corresponding oxidation products with precipitation of the catalyst, removing said precipitated catalyst by centrifugation or filtration and recycling said catalyst to said oxidation.

2. The process as claimed in claim 1, wherein the substrates which react with $^1O_2$ are olefins which contain 1 to 10 C=C double bonds; $C_6$–$C_{50}$ phenols, polyalkylbenzenes, polyalkoxybenzenes; polycyclic aromatics having 2 to 10 aromatic rings; alkyl sulfides, alkenyl sulfides, aryl sulfides which are either mono- or disubstituted on the sulfur atom, and $C_4$–$C_{60}$ heterocycles having an O, N or S atom in the ring, which may be unsubstituted or may be mono- or polysubstituted by halogens, cyanide, carbonyl groups, hydroxyl groups, $C_1$–$C_{50}$ alkoxy groups, $C_1$–$C_{50}$ alkyl groups, $C_6$–$C_{50}$ aryl groups, $C_2$–$C_{50}$ alkenyl groups, $C_2$–$C_{50}$ alkynyl groups, carboxylic acid groups, ester groups, amide groups, amino groups, nitro groups, silyl groups, silyloxy groups, sulfone groups, sulfoxide groups or by one or more $NR^1R^2$ radicals in which $R^1$ or $R^2$ may be identical or different and are H; $C_1$–$C_{50}$ alkyl; formyl; $C_2$–$C_{50}$ acyl, $C_7$–$C_{50}$ benzoyl, where $R^1$ and $R^2$ may also together form a ring.

3. The process of claim 1, wherein the reaction temperature is between 0 and 50° C.

4. The process of claim 2 wherein the reaction temperature is 15 to 35° C.

5. The process of claim 1 wherein 2 to 10 equivalents of $H_2O_2$ are used depending on the substrate used.

* * * * *